(12) United States Patent
Buchmeyer

(10) Patent No.: US 9,451,922 B2
(45) Date of Patent: Sep. 27, 2016

(54) RADIATION PROTECTION ARRANGEMENT

(71) Applicant: MAVIG GMBH, Munich (DE)

(72) Inventor: Markus Buchmeyer, Munich (DE)

(73) Assignee: MAVIG GMBH, Munich (DE)

( * ) Notice: Subject to any disclaimer, the term of this patent is extended or adjusted under 35 U.S.C. 154(b) by 0 days.

(21) Appl. No.: 14/434,448

(22) PCT Filed: Oct. 8, 2013

(86) PCT No.: PCT/EP2013/070977
§ 371 (c)(1),
(2) Date: Apr. 9, 2015

(87) PCT Pub. No.: WO2014/056940
PCT Pub. Date: Apr. 17, 2014

(65) Prior Publication Data
US 2015/0272519 A1   Oct. 1, 2015

(30) Foreign Application Priority Data
Oct. 9, 2012 (DE) .................. 10 2012 218 391

(51) Int. Cl.
*A61N 5/00* (2006.01)
*A61B 6/10* (2006.01)
(Continued)

(52) U.S. Cl.
CPC ................. *A61B 6/107* (2013.01); *A61B 6/04* (2013.01); *A61B 90/50* (2016.02); *A61N 5/10* (2013.01);
(Continued)

(58) Field of Classification Search
USPC ......... 250/505.1, 506.1, 515.1, 516.1, 518.1, 250/519.1
See application file for complete search history.

(56) References Cited

U.S. PATENT DOCUMENTS

| 4,062,518 A | 12/1977 | Stivender et al. |
| 5,900,638 A | 5/1999 | Jaeger et al. |

(Continued)

FOREIGN PATENT DOCUMENTS

| DE | 1466848 | 2/1969 |
| DE | 1516420 | 8/1969 |

(Continued)

OTHER PUBLICATIONS

International Search Report dated May 28, 2014 issued in PCT/EP2013/070977.
(Continued)

*Primary Examiner* — Nicole Ippolito
(74) *Attorney, Agent, or Firm* — Scully Scott Murphy and Presser; Frank Digiglio

(57) ABSTRACT

A radiation protection arrangement, in particular for attachment to at least one support rail which is preferably attached with a fastening device to one or more sides of the treatment table, comprising a fastening device at the at least one lamella which comprises a material for protection against radiation, preferably X-ray radiation, is preferably pivotably mounted, wherein the fastening device comprises a holder which can be attached to the support rail, wherein the holder comprises: at least one pivotably mounted handle, the handle having a free end and an end on which the handle is pivotably mounted, a locking mechanism suitable for locking the holder on the support rail, wherein the locking mechanism can be actuated by a pivotal movement of the at least one handle that is pivotably mounted on the holder.

The invention further relates to a radiation protection arrangement, in particular for attachment to at least one support rail which is preferably attached to one or more sides of the treatment table, comprising a holder which can be attached to the support rail and at least one detachable lamella which can be attached to the holder at various positions, the radiation protection arrangement being preferably combinable with one of the preceding radiation protection arrangements.

23 Claims, 7 Drawing Sheets

(51) Int. Cl.
*G21F 3/00* (2006.01)
*A61B 6/04* (2006.01)
*A61N 5/10* (2006.01)
*A61G 13/10* (2006.01)
*A61G 7/05* (2006.01)

(52) U.S. Cl.
CPC ........... *G21F 3/00* (2013.01); *A61B 2090/571* (2016.02); *A61G 13/10* (2013.01); *A61G 2007/051* (2013.01); *A61G 2210/50* (2013.01); *A61N 2005/1094* (2013.01)

(56) References Cited

U.S. PATENT DOCUMENTS

| | | | |
|---|---|---|---|
| 2012/0241652 A1 | 9/2012 | Jeschke | |
| 2014/0029720 A1* | 1/2014 | Osherov | A61B 6/548 |
| | | | 378/62 |

FOREIGN PATENT DOCUMENTS

| | | | |
|---|---|---|---|
| DE | 2749826 | A1 | 5/1978 |
| DE | 3012463 | A1 | 10/1981 |
| DE | 3326880 | A1 | 2/1985 |
| DE | 29704613 | U1 | 7/1997 |
| DE | 10325567 | A1 | 1/2005 |
| DE | 102009025380 | A1 | 12/2010 |
| DE | 102009057366 | A1 | 6/2011 |
| WO | WO 01/84558 | A1 | 11/2001 |
| WO | WO 2004/107979 | A1 | 12/2004 |

OTHER PUBLICATIONS

English Abstract of WO 2010146109 A1, dated Dec. 23, 2010.
English Abstract of WO 2004/107979 A1, dated Dec. 16, 2004.

* cited by examiner

RADIATION PROTECTION ARRANGEMENT

The invention relates to a radiation protection arrangement, in particular for attachment to a support rail which is mounted on the side of a treatment table, as lower body protection. This radiation protection arrangement is in particular suitable for use in interventional radiology and during surgery serves to protect the staff involved, such as the physician or assistants, from radiation, in particular X-ray radiation.

DE 10 2009 025 380 A1 relates to a radiation protection arrangement, in particular for attachment to a support rail which is mounted on the side of a treatment table. The radiation protection arrangement comprises at least one lamella made from a radiation protection material and an associated fastening device. The lamella is pivotably mounted on the fastening device. The fastening device comprises a holder which is attachable to the support rail and, with a locking device the holder can be fastened to the support rail.

WO 2004/107979 relates to a radiation protection arrangement that can be laterally attached to a medical examination or treatment table as lower body protection. One embodiment of this radiation protection arrangement comprises a plurality of lamellae mounted side by side, which at one end are fastened to a common supporting element. Additionally, an upper part is provided that is attachable to the support rail on the treatment table. In this known radiation protection arrangement, the lamellae may consist of a lead rubber mat which may, for example, comprise lead foils layered in PVC. The lead rubber mats are inserted into covers consisting of an easily cleanable and sterilizable material. The length of the lamellae can be changed by folding upward a lower end and fixing said end in this folded-up position, for example by means of press buttons, velcro fastener or the use of straps.

DE 1 516 420 describes a radiation protection arrangement having a plurality of individual lead rubber flaps which are pivotably mounted. Each lead rubber flap is pivotably mounted about an axis vertical thereto and situated above its center of gravity. One embodiment comprises a comb-like support having pins at its extensions, with the individual lead rubber flaps being pivotably mounted on said pins.

DE 1 466 848 describes a radiation protection arrangement wherein lead rubber flaps are attached via rotary axes on the lateral edge of a fluorescent screen support.

DE 27 49 826 A1 describes an X ray shielding device comprising lead rubber flaps which are pivotably mounted about axes by means of clamps. In one embodiment, a slide rail has a T-shaped inner profile into which holders are insertable.

DE 30 12 463 C2 discloses a radiation protection arrangement wherein lead rubber flaps are pivotably suspended on a support. In one embodiment, a supporting element has comb-like extensions on which the lead rubber flaps are mounted in an articulated manner.

DE 279 04 613 U1 describes a radiation protection arrangement wherein individual lead rubber flaps can be pivotably attached to a rail. In one embodiment, a support is provided for each lead rubber flap, said support being adjustably supported in a guide rail. The lead rubber flaps are pivotably mounted on a support about a transverse axis. Furthermore, braking means are provided which prevent that the supports are unintentionally displaced within the rail. Alternatively, a catch or a locking device can be used for this purpose. In a further embodiment, each lead rubber flap comprises an eyelet with a through hole, on which the lead rubber flaps are held by a pivot axis.

It is the object of the invention to provide a radiation protection arrangement which is easily attachable to a treatment table and easy to manage. Furthermore, it is an object of the invention to provide a simple and secure fastener for the locking mechanism of the radiation protection arrangement on the treatment table, as well as a comfortable carrying system of the radiation protection arrangement.

This object is achieved with a radiation protection arrangement according to the patent claims.

The radiation protection arrangement of the invention is in particular suitable for attachment to a support rail which is attached to the side of a treatment table.

The invention is based on the basic idea of locking a radiation protection arrangement comprising an associated holder by a suitable mechanism at a desired position on the support rail of the treatment table, in order to prevent slipping of the radiation protection arrangement, with the mechanism being activated by means of one or more handles.

The handle(s) is/are used by the technical staff for comfortably carrying the radiation protection arrangement and, as soon as the radiation protection arrangement is attached to the support rail, it is possible to actuate the mechanism with a simple pivoting motion of the handle(s) and thus to lock the radiation protection arrangement on the support rail.

The invention has the advantage that it allows to quickly and reliably perform the secure locking of the radiation protection arrangement on the support rail. It is not necessary to set down the radiation protection arrangement for locking. During locking there is always at least one hand of the technical staff on the radiation protection arrangement. Thus, an unintentional dropping of the radiation protection arrangement can be prevented.

The invention also has the advantage that it is possible during locking of the radiation protection arrangement on the support rail to prevent the risk of injury of the technical staff by an injury during locking, such as crushing the fingers of the technical staff. Furthermore, the carrying of the radiation protection arrangement away from the treatment table or toward the treatment table becomes comfortable.

The handle(s) is/are preferably attached to the side of the radiation protection arrangement so that the use of turning handles or other mounting devices on the side of the radiation protection arrangement facing the technical staff is not required for this locking. Consequently, the technical staff will not bump into such turning handles or the like.

When carrying the radiation protection arrangement, the handle(s) is/are preferably turned up into a position at an angle of 10° to 70°, preferably of 30°, relative to the longitudinal direction of the holder, so that the technical staff suffers from as little load at the wrist as possible and optimal carrying comfort can be ensured.

The invention relates to a radiation protection arrangement, in particular for attachment to at least one support rail which is preferably attached at one or more sides of a treatment table, having a fastening device at the at least one lamella which has a material for shielding against radiation, preferably X-ray radiation, which is preferably pivotably mounted, wherein the fastening device comprises a holder that can be attached to the support rail, wherein the holder comprises: at least one pivotably mounted handle, the handle having a free end and an end on which the handle is pivotably mounted, a locking mechanism suitable for locking the holder on the support rail, the locking mechanism being activatable by a pivoting motion of the at least one handle which is pivotably mounted on the holder.

The one or more sides of the treatment table comprise(s) both the long side and the narrow side of the treatment table. In addition, one or more lamellae can be securely attached to the fastening device or at least one can be pivotably mounted or at least one can be gimbal-mounted on the fastening device. Furthermore, any combination of the options for the arrangement or suspension of the one or more lamellae is possible.

In a further embodiment, the at least one handle is in direct operative connection with the locking mechanism. In this connection, a direct operative connection means that the handle is directly adjacent to the locking mechanism and that by its operation, for example a movement of the handle, the locking mechanism is triggered.

In a further embodiment, the locking mechanism comprises at least one locking bolt which is suitable to lock the holder of the radiation protection arrangement on the support rail. The locking bolt may have a rectangular base or the base of a parallelogram with a particular height or of a cylinder, preferably a circular cylinder.

In a further embodiment, the handle is suitable for being pivoted into a first position. In the first position, the holder on the support rail is not locked by means of the locking bolt.

In a further embodiment, the handle is suitable for being pivoted into a second position. In the second position, the at least one locking bolt locks the holder on the support rail.

In a further embodiment, the holder comprises a longitudinal profile and a receptacle, the longitudinal profile has a contact face, and when the radiation protection arrangement is attached to the support rail, the contact face of the longitudinal profile partially rests on the upper side of the support rail, and the at least one locking bolt is preferably situated in the receptacle which is arranged on the contact face of the longitudinal profile such that the at least one locking bolt is situated at a specific distance A from the contact face.

In a further embodiment, the distance A is designed such that when the radiation protection arrangement is attached to the support rail, the locking bolt in a locked state extends partially along the bottom of the support rail. The distance A can be identical to the thickness A' of the support rail or greater than the thickness A' of the support rail, preferably from 0.05 to 3.0 mm greater, and further preferably from 0.5 to 1.5 mm greater.

In a further embodiment, the distance A is designed such that when the radiation protection arrangement is attached to the support rail, the locking bolt in the locked state is pressend onto the bottom of the support rail, preferably at an angle of from 30° to 60°, preferably 45° to the normal of the bottom of the support rail. The locking bolt may also be designed such that the locking bolt is pressed onto the edge of the support rail closest to the locking bolt at an angle of from 30° to 60°, preferably of 45° to the normal of the bottom.

In a further embodiment, the longitudinal profile has a short and a long side and the handle is suitable for being pivoted to and fro between the first and the second position in parallel to the long side of the longitudinal profile of the holder.

In a further embodiment, the longitudinal profile has on one side at least one recess, preferably a V-shaped one. Furthermore, the tapered end of a V-shaped recess may be rounded. Such rounding of the tapered end of the recess can in particular ensure that the radiation protection arrangement is variably positionable on the support rail.

In a further embodiment, the handle is arranged in the first position at an angle of from 10° to 70°, preferably 30°, to the longitudinal direction of the longitudinal profile of the holder with respect to the upper side of the longitudinal profile.

In a further embodiment, the handle is arranged in the second position in a position at an angle of approximately −90° to the longitudinal direction of the longitudinal profile of the holder with respect to the upper side of the longitudinal profile.

In a further embodiment, the handle is attached to the short side of the longitudinal profile.

In a further embodiment, the holder has a bearing in which the handle is pivotably mounted.

In a further embodiment, the handle has at least one latching recess which is suitable for retaining the handle in the first and/or the second position up to a particular gravitational force.

In a further embodiment, the handle comprises an anti-sliding device which is suitable for preventing that a hand slides from the handle in the second position, with the anti-sliding device being preferably formed as projection at the free end of the handle.

In a further embodiment, the locking mechanism comprises a displaceable rod.

The invention also relates to a radiation protection arrangement, in particular for attachment to at least one support rail which is preferably attached to one or more sides of a treatment table, with a holder that can be attached to the support rail and at least one detachable lamella which can be attached at various positions on the holder, with the radiation protection arrangement being preferably combinable with one of the above radiation protection arrangements.

In one embodiment, the holder comprises at least one bore and the at least one detachable lamella comprises at least one pin. The at least one pin is insertable into the at least one bore.

According to a further embodiment, the at least one detachable lamella comprises at least one, preferably U-shaped, holding means. The at least one U-shaped holding means can be designed such that it is attachable to the holder in a form-locking and/or a force-locking manner. The at least one, preferably U-shaped, holding means may preferably be made from a plastic material, especially preferably in the form of plastic clips. The at least one detachable lamella with the preferably U-shaped holding means may be designed such that it is preferably slidingly displaceable on the longitudinal profile of the radiation protection arrangement. The U-shaped holding means and the sliding displaceability allow a variable attachment and facilitate handling. Moreover, the risk of any paint damage to the longitudinal profile of the radiation protection arrangement is minimized.

The detachable lamella with the at least one U-shaped holding means can be attached both to holders with bores and holders without bores.

The term "treatment table" also comprises all kinds of patient-supporting tables, examination tables or operating tables.

According to a further embodiment, the radiation protection arrangement may also comprise at least one transverse lamella comprising a material for protection against radiation, preferably X-ray radiation. The material for protection against radiation, in particular X-ray radiation, may in particular be the same material as that of the at least one lamella which is preferably pivotably attached. The at least one transverse lamella can be attached to the fastening device. In particular, the at least one transverse lamella can be attached to the inside and/or the outside of the wall of the longitudinal profile, which faces away from the treatment table. The transverse lamella is preferably attached such that it at least partially extends along the long side of the longitudinal profile. In particular, the transverse lamella can be attached to the longitudinal profile such that, when the at least one lamella makes any pivotal movements, it completely covers the fastening device and the part of the at least one lamella which is suspended on the fastening device. Furthermore, the accordingly designed at least one transverse lamella can ensure additional protection in cases of rotary movements of the handle(s). The transverse lamella can be screwed, riveted or stuck together with the longitudinal profile. Furthermore, the transverse lamella can be attached to the same fastening device as the at least one lamella. Thus both the lamella and the transverse lamella may each have an eyelet, and the transverse lamella and the at least one lamella are attached to the same fastening device. The fastening device may be formed as a screw, to which the eyelets are attached, and the lamella and the transverse lamella are accordingly secured by a screw nut. When a plurality of lamella is used, the transverse lamella can be attached to all fastening devices of the plurality of lamellae or to just a part thereof, for example, in the case of five lamellae, they can be attached to the two outer fastening devices as well as to the central one. Furthermore, the transverse lamella can be attached to the side of the support facing away from the treatment table. Furthermore, in the case of more than two transverse lamellae, the transverse lamellae can be overlappingly attached. The transverse lamella may be attached to the support such that, in the direction of the treatment table, it completely covers the fastening device of the at least one lamella as well as the part of the at least one lamella that is suspended on the fastening device. In particular, when detachable lamellae are used—which are attached in such a way, and preferably have such dimensions, that when the lower end portions of the detachable lamellae are aligned overlappingly with the upper end portions of the lamellae, the end portions of the lamellae are not covered—it can be ensured that no radiation penetrates through this region. Furthermore, the use of the at least one transverse lamella makes it possible to do without a detachable lamella, if necessary.

In the following, the invention will be described in more detail on the basis of examples and the drawings.

Figure 1:
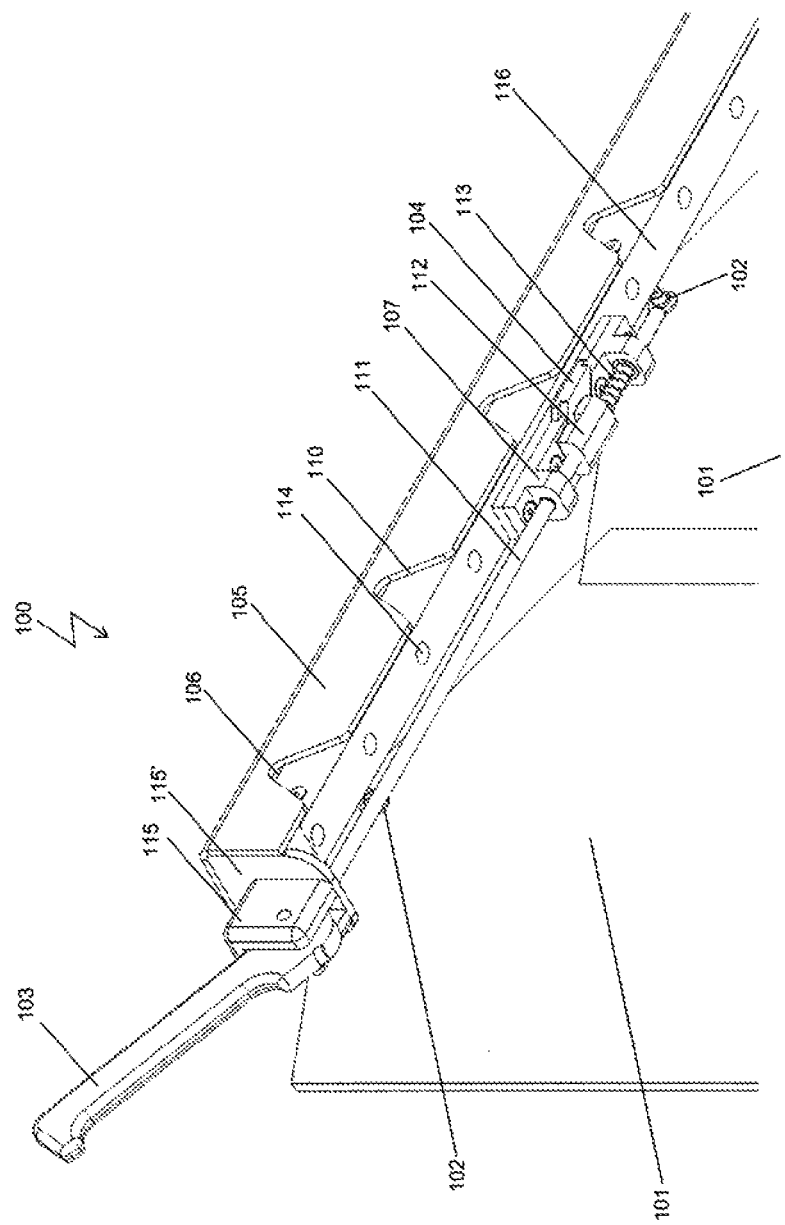
FIG. 1 shows a perspective view of a preferred embodiment of a radiation protection arrangement according to the invention.

FIG. 1 shows an embodiment of a radiation protection arrangement 100 according to the present invention for attachment to a treatment table. In the example shown in FIG. 1, two lamellae 101 are each arranged at a corresponding fastening device 102. The radiation protection arrangement 100 further comprises a holder, the holder in turn having a longitudinal profile 105. The longitudinal profile 105 has a short and a long side. Laterally to the short side of the longitudinal profile 105, a handle 103 is pivotably mounted in a holder 115 about a pivotal axis 115b. According to the present embodiment, the holder 115 is connected to the longitudinal profile 105 by a corresponding connecting element 115'. The longitudinal profile 105 further comprises a contact face 106. When attached to a support rail 200 (see FIG. 5), the radiation protection arrangement 100 partially rests with the contact face 106 of the longitudinal profile 105 on the upper side of the support rail 200. Furthermore, on the side facing the treatment table, the longitudinal profile 105 has one or more V-shaped recesses 110 into which corresponding pins 201 (see FIG. 5) of the support rail 200 extend in the attached state. Thus, it can be prevented that the radiation protection arrangement 100 is unintentionally displaced in the lateral direction along the support rail 200 and/or the treatment table. Furthermore, the holder comprises a support 116 wherein bores are provided that are evenly spaced in the vertical direction. Bores with identical diameters are identically found also in the longitudinal profile 105. In the attached state of the radiation protection arrangement 100, it is possible to additionally attach upwardly extending lamellae 118 (see FIG. 5) through these bores. This ensures radiation protection in the area of the upper body of the technical staff, see FIG. 5.

FIG. 1 shows the radiation protection arrangement 100 in the unlocked, i.e. the open state, ready for attachment to the support rail 200. In the open state, the locking bolt 104 does not, or only to a very small degree, project beyond the support 116 in the direction of the support rail 200. In this way, the radiation protection arrangement 100 can be attached to the support rail 200 such that the support rail 200 is located between the support 116 and the inner side of the longitudinal profile 105 facing the treatment table. The handle 103 is turned up in the unlocked state and is situated at a angle in relation to the long side of the longitudinal profile of the holder in the direction of a first position, an open position. This angle is preferably from 10° to 70°, especially preferably 30°. Consequently, when carrying the radiation protection arrangement 100, as little load as possible is applied to the wrist of the technical staff and it is possible to ensure optimal carrying comfort.

As shown in FIG. 1, the handle 103 is in operating connection with a connecting rod 111 which extends in a receptacle 107. The handle 103 in the holder 115 pivots downward into a second position about the rotation axis 115b.

The front face of the handle 103 is formed as a cam 115a on the side on which the handle 103 is connected with the rotation axis 115b at the holder 115'. In the longitudinal direction of the longitudinal profile, the cam 115a presses the connecting rod 111 inward against a spring 113. The spring ensures that the handle 103 in its unlocked state is retained in its first position and does not unintentionally swivel. Additionally, a slider 112 which is in connection with a locking bolt 104 is fastened to the connecting rod 111. The locking bolt 104 has the base of a parallelogram and a specific height, so that the base of the locking bolt 104 has a long side and a short side. The long side is displaced at an angle of 45° to the support 116. The locking bolt 104 is slidably provided in the receptacle by means of a tongue-and-groove connection. The height of the locking bolt 104 is dimensioned such that the locking bolt is not flush with the surface of the receptacle 107. Therefore, it is possible for the slider 112 which has a recess corresponding to the locking bolt 104, likewise at an angle of 45°, to enter into an operating connection with the locking bolt. The operating connection is designed such that when the connecting rod 111 is moved, the slider 112 presses the locking bolt 104 in the tongue-and-groove connection outwardly with respect to the longitudinal profile. The movement of the connecting rod 111 is caused by pivoting the end of the handle 103 that is formed as cam 115a. Thus, a locking mechanism is provided wherein the pivoting movement of the handle 103 leads to a movement of the locking bolt 104 and eventually to the locking of the radiation protection arrangement 100 at a support rail 200. The support 116 and the receptacle 107 are dimensioned such that when the radiation protection arrangement 100 is attached to the support rail 200, the locking bolt 104 in the locked state extends partially or completely along the bottom of the support rail 200. The distance of the locking bolt 104 to the bottom of the support rail 200 is preferably from 0 to 1 mm, further preferably 0.5 mm. The radiation protection arrangement 100 is locked with the support rail 200 so that the radiation protection arrangement 100 cannot unintentionally detach itself from the support rail 200.

The handle 103 further comprises an anti-sliding device 109 which is provided at its free end, i.e. opposite the end to which the handle is pivotably attached in the holder 115. The handle 103 further comprises latching recesses. In FIG. 1 only one latching recess 108 is shown. When the handle 103 is in a position in which a latching recess is in contact with an edge of the holder 115, the handle is fixed in this position such that this position can only be released by overcoming a certain resistance, i.e. by overcoming a certain pivot force.

Figure 2:
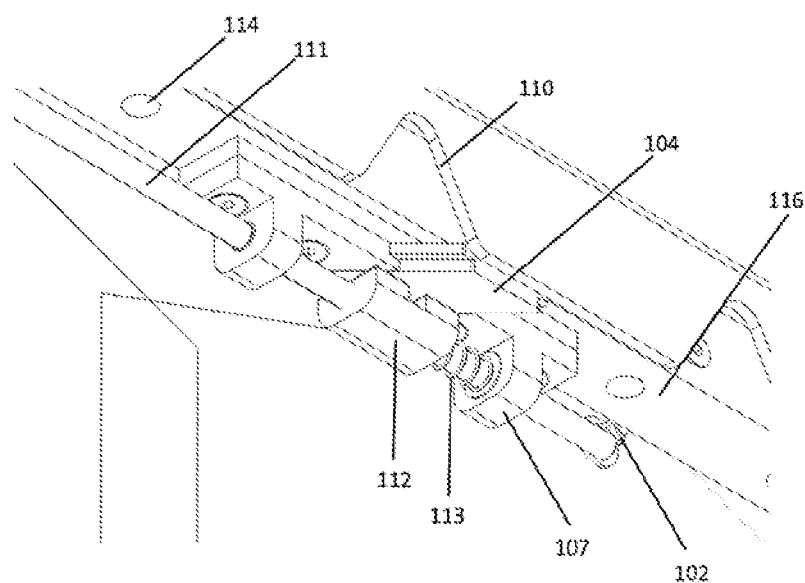
FIG. 2 shows an enlarged partial view of the perspective view of FIG. 1.

FIG. 2 shows a perspective partial view of a section of the radiation protection arrangement 100 of the first preferred embodiment according to the present invention. In particular, it shows the connecting rod 111, the slider 112 attached to the connecting rod 111, the locking bolt 104 which is in communication with the slider 112 and attached to the receptacle 107 by a tongue-and-groove mechanism, and the support 11. It further shows the return spring 113 which is suitable for retaining the handle 103, which is in operating connection with the connecting rod 111, in the open position, i.e. the first position, by suitable pressure on the slider 112.

Figure 3:
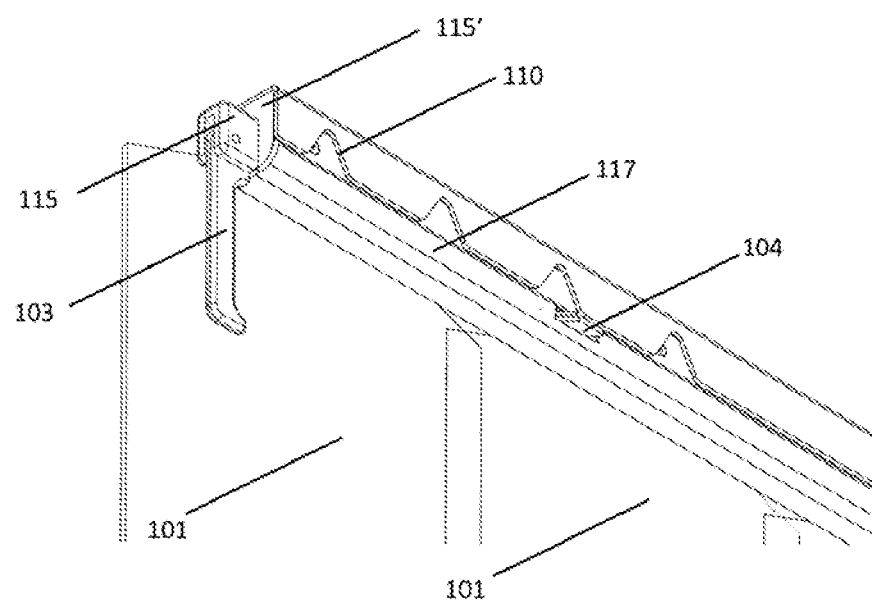
FIG. 3 shows a further perspective view of the first preferred embodiment of a radiation protection arrangement according to the present invention.
Figure 4:
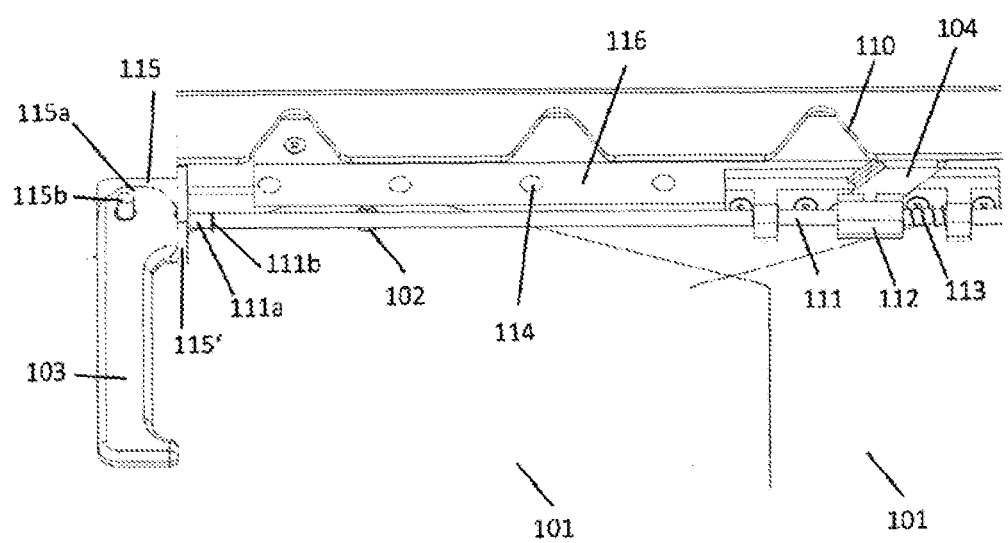
FIG. 4 shows a front view of the first preferred embodiment of a radiation protection arrangement according to the present invention.

FIGS. 3 and 4 show a perspective view of the first preferred embodiment of a radiation protection arrangement according to the present invention. In contrast to FIG. 1 and FIG. 2, a protective cover 117 is provided over the connecting rod 111, the spring 113, the receptacle 107, the slider 112, as well as over part of the locking bolt 104. A corresponding recess is provided in the protective cover 117 so that the locking bolt 104 can move freely in the lateral direction and project from the protective cover 118. In FIGS. 3 and 4, in contrast to FIGS. 1 and 2, the radiation protection arrangement 100 is in the locked state. The locking bolt 104 projects beyond the support 116 in the direction of the support rail 200 and/or the treatment table (both not shown) beyond the support 116. When the radiation protection arrangement 100 is in this state attached to a support rail 200, it is possible in this second, closed position of the handle 103, to arrange the locking bolt 104 such that it partly or completely extends over the bottom of the support rail 200. The radiation protection arrangement is thereby locked and prevented from any unintentional dropping. The second, closed position of the handle 103 is directed downward, at an angle of about −90° with respect to the longitudinal direction of the longitudinal profile 105. The handle 103 is located in a corresponding recess of the holder 115 so that the handle 103 is flush with one side of the holder 115. However, according to the invention it is also possible that, in a closed position, the handle 103 is even further pivoted into the holder so that the handle 103 is situated in a corresponding recess thereof and is flush with the bottom of the holder.

In the embodiment shown in FIG. 4, the connecting rod 111 comprises a securing ring 111b which is arranged at a short distance from the end of the connecting rod 111 such that, in the unlocked state of the handle 103, the securing ring 111b forms an attachment point of the connecting rod 111 at the connecting element 115'. Furthermore, at its end which is in contact with the cam 115a, the connecting rod 111 has an end section 111a. The end section 111a of the connecting rod is preferably formed as a spherical head and consists of a preferably self-lubricating and/or sliding material. A suitable material may, e.g., be brass or teflon (PTFE).

Figure 5:
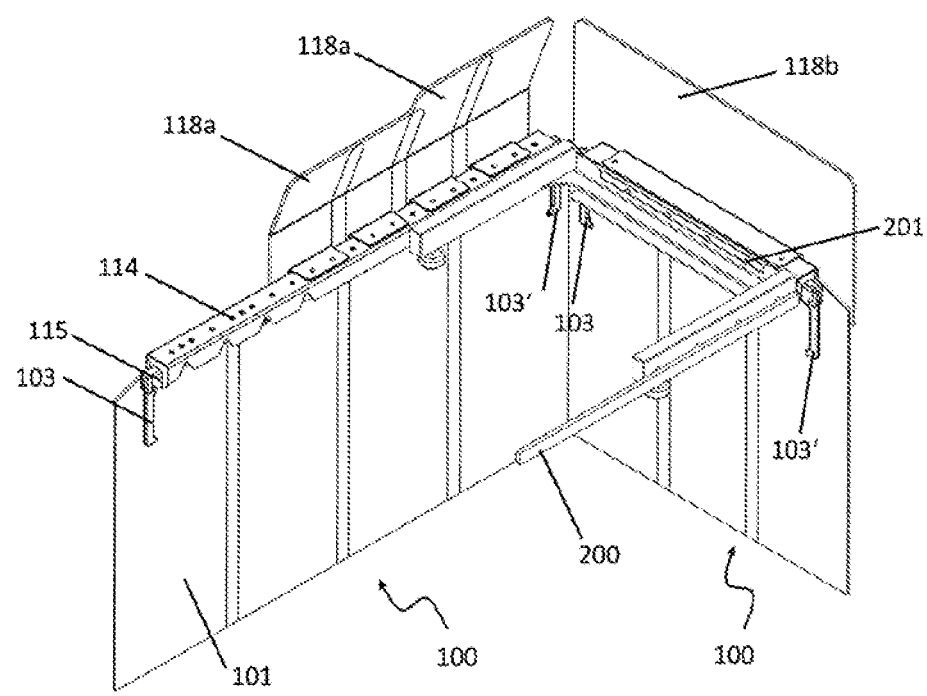
FIG. 5 shows a perspective view of a set of two radiation protection arrangements in the locked state on a support rail on the side and at the head section of a treatment table (not shown) according to a second preferred embodiment of the present invention.

FIG. 5 shows a set of two radiation protection arrangements 100 in the locked state at the support rail 200 in the lateral section and the head section of a treatment table according to a second embodiment of the present invention. In this second embodiment, a radiation protection arrangement 100 with two handles 103, 103' is provided at both the short side and the long side of the longitudinal profile. In this case, the handle 103 and the first handle 103' are in communication with a locking mechanism according to the first preferred embodiment, as described in FIGS. 1 to 4 above. Thus, each radiation protection arrangement 100 comprises at least one locking bolt, two handles and two holders.

According to the invention, support rails 200 can be attached to all long and short sides of a treatment table, and thus also at the tail end of the treatment table. Furthermore, the support rail 200 may be interrupted om one or more sides of the treatment table or a plurality of support rails 200 may be attached to one or more equal sides of the treatment table. According to the invention it is possible to attach a plurality of radiation protection arrangements 100 next to each other to one or more equal sides of the treatment table, for example to attach two radiation protection arrangements 100 next to each other to the longitudinal side of the treatment table.

As shown, it is possible to additionally provide first detachable lamellae 118a and second detachable lamellae 118b (one shown) for protecting the upper body of the technical staff against radiation. The first detachable lamellae 118a are arranged at the long side of the treatment table, have a bend in the direction toward the treatment table, and are designed in the two-part form. The second detachable lamella 118b is broader and has a straight basic form. It is arranged at the short side of the treatment table. The first detachable lamellae 118a and the second detachable lamellae 118b are preferably attached and preferably have dimensions such that when the lower end portions of the detachable lamellae 118a, 118b are overlappingly aligned with the upper end sections of the lamellae 101, the end sections of the lamellae 101 are covered. The detachable lamellae 118a, 118b have one or more pins (not shown) on their bottom, which are suitable for being inserted into bores 114 at the upper side of the holder. The detachable lamellae 118a and 118b can be mounted in another manner on the holder and/or the longitudinal profile 105, preferably by means of U-shaped holding means, which are further explained in the following.

The bores 114 have, for example, alternating distances; however, according to another embodiment, they may also have equal distances. Thus, the bores 114 form a row of bores on the radiation protection arrangement 100 or on the radiation protection arrangements 100 arranged next to each other, so that the detachable lamellae 118*a*, 118*b* can be variably arranged along the row of bores. Therefore, it is, for example, possible to displace a detachable lamellae 118*a*, 118*b* during surgery such that a gap is formed between two detachable lamellae 118*a*, 118*b* through which the patient can be treated. After treatment, this gap may be closed again by returning the displaced detachable lamella 118*a*, 118*b* to its original position.

According to the invention it is also possible to replace the row of bores 114 by other means for arranging and retaining the detachable lamellae 118*a*, 118*b*. For example, each detachable lamella 118*a*, 118*b* may comprise a fastening device that can be fastened on the holder in a form-locking and/or a force-locking manner. For example, the fastening device has a U-profice which is attachable to the longitudinal profile 105. Preferably, the U-profile is formed like a bracket and comprises latching means which can, for example, be releasably brought into engagement with a latching groove on the outside of the longitudinal profile 105. Here it is advantageous if at least one latching groove or the protrusion or recess consists of an elastic material, such as a plastic.

The bolts 201 of the support rail 200 project into the V-shaped recesses 110 of the radiation protection arrangements 100 so that it is possible to prevent any longitudinal displacement of the radiation protection arrangement 100 on the support rail 200.

In a further embodiment, the radiation protection arrangement 100 comprises two pivotable handles 103, 103'. However, only the handle 103 is in operating connection with a locking mechanism. The other handle 103' is merely pivotably mounted in the holder 115' and may correspondingly be pivoted into the first and the second position without, however, thereby activating a locking mechanism.

By using a variable attachment of the radiation protection arrangement 100 to the support rail 200 by means of the above described locking and the use of the variable arrangement of detachable lamellae 118*a*, 118*b* on the holder of the radiation protection arrangement, it is ensured that the operating and/or technical staff is perfectly protected from radiation while simultaneously radiation protection is adapted to the needs of the operating and/or technical staff and/or to the specific circumstances of the individual treatment of the patient.

Figure 6A:
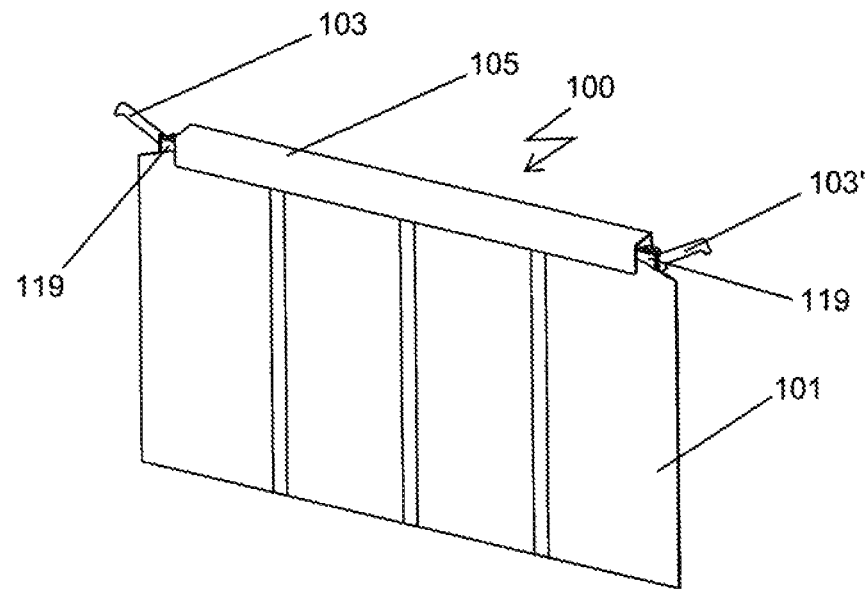
FIGS. 6a and 6b show a perspective view of a radiation protection arrangement according to a third preferred embodiment of the present invention.
Figure 6B:
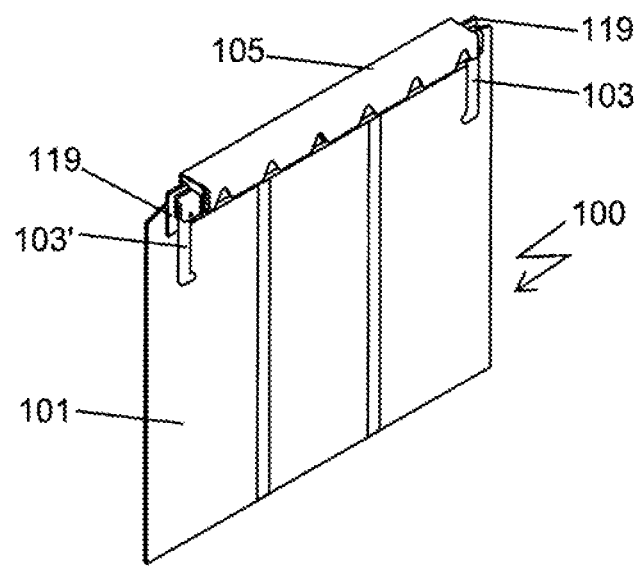

FIGS. 6*a* and 6*b* show perspective views of a radiation protection arrangement according to a third preferred embodiment of the present invention. In the example shown, the radiation protection arrangement 100 comprises four lamellae 101, each of which is attached to a corresponding fastening device. The radiation protection arrangement 100 further comprises a holder, which holder in turn comprises a longitudinal profile 105. On both sides of the longitudinal profile 105, a handle 103 or 103' is pivotably mounted laterally on the short side. Furthermore, the radiation protection arrangement 100 comprises a transverse lamella 119 which is attached to the support 116 (not shown) in parallel to the long side of the longitudinal profile 105. In the embodiment, the lamellae 101 have a triangular form in the section of the upper end, which tapers triangularly in the direction of the fastening device. The transverse lamella 119 is attached and designed such that it overlaps the upper part of the lamellae 101 in the direction of the treatment table. Preferably, the transverse lamella 119 covers the zone in which the upper part of the lamellae 101 is connected to the fastening device. In the example shown in FIGS. 6*a* and 6*b*, the longitudinal profile 105 does not have any bores 114.

Figure 7A:
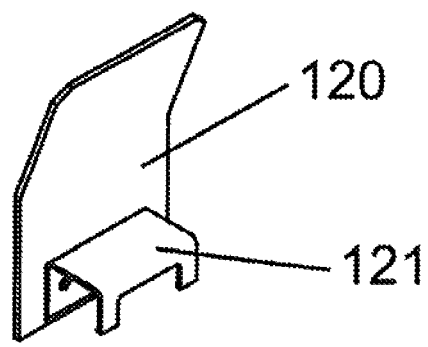
FIG. 7a shows a perspective view of a detachable lamella according to a preferred embodiment of the present invention.

FIG. 7*a* shows a detachable lamella 120 according to a further preferred embodiment of the present invention. A holding means 121 which has a U-shaped profile is attached to the detachable lamella 120, the holding means preferably consisting of a plastic. By means of this U-shaped holding means 121, the detachable lamella 120 can be attached to the radiation protection arrangement 100 in a form-locking and/or force-locking manner. In the present example, a recess is cut out of the holding means with its U-shaped profile on the side facing the treatment table, so that on this side only two bars are found. These two bars reach around the side of the longitudinal profile 105 facing the treatment table so that a stable holding means is ensured. On the longitudinal profile, the detachable lamella 120 can be slidingly displaced in the longitudinal direction.

Figure 7B:
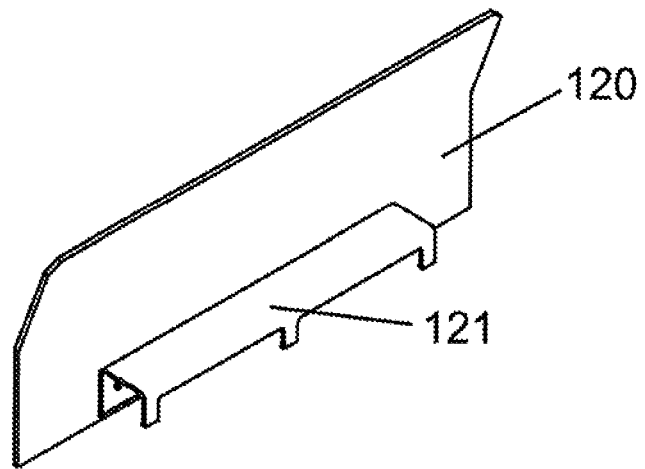
FIG. 7b shows a perspective view of a detachable lamella according to a further embodiment of the present invention.

FIG. 7*b* shows a detachable lamella 120 according to a further preferred embodiment of the present invention. Compared with the detachable lamella in FIG. 7*a*, the detachable lamella in the example shown in FIG. 7*b* is wider in the longitudinal direction, by way of example by a factor 3. Accordingly, the holding means 121 in the example shown in FIG. 7*b* is also longer in the longitudinal direction. On the side facing the treatment table, the holding means 121 has two recesses so that three bars are formed. These three bars clamp the side of the longitudinal profile 105 facing in the direction of the treatment table so that it is possible to ensure a secure fit of the detachable lamella on the longitudinal profile 105. According to the present invention, the holding means 121 may also have only one or even more than three bars. Thus, the number and/or the width of the bars can be selected and/or varied depending on the desired clamping force of the holding means 121.

Also in the embodiment shown in FIG. 7*b*, the detachable lamella can be slidingly displaced in the longitudinal direction on the longitudinal profile 105 of the radiation protection arrangement 100.

Although the invention has been illustrated and described in detail on the basis of the Figures and the corresponding description, this illustration and this detailed description should be understood to be illustrative and exemplary and not as restricting the invention.

It is clear that persons skilled in the art may make changes and modifications without leaving the scope and the spirit of the following claims. In particular, the invention also encompasses embodiments with any combination of features mentioned or shown above or below with respect to various embodiments.

The invention also encompasses individual features in the Figures even if they are shown therein in connection with other features and/or are not mentioned above or below. Furthermore, the alternatives of embodiments described in the Figures and the description as well as individual alternatives may be excluded from the subject-matter of the invention and/or the disclosed subject-matters. The disclosure encompasses embodiments which exclusively comprise the features described in the claims and/or in the embodiments as well as embodiments comprising other additional features.

The invention claimed is:

1. A radiation protection arrangement for attachment to at least one support rail, which is attached to one or more sides of a treatment table, comprising
   a fastening device on at least one lamella which comprises a material for protection from radiation and which is pivotably mounted, wherein the radiation protection arrangement further comprises a holder which can be attached to the support rail, wherein the holder comprises:
   at least one pivotably mounted handle, the handle having a free end and an end on which the handle is pivotably mounted,
   a locking mechanism suitable for locking the holder on the support rail, the locking mechanism being operable by a pivoting motion of the at least one handle which is pivotably mounted on the holder,
   a longitudinal profile, wherein the longitudinal profile has a short and a long side, the handle is attached to the short side of the longitudinal profile and wherein the handle is capable of being pivoted to and fro in parallel to the long side of the longitudinal profile of the holder.

2. The radiation protection arrangement according to claim 1, wherein the at least one handle is in direct operative connection with the locking mechanism.

3. The radiation protection arrangement according to claim 1, wherein the locking mechanism comprises at least one locking bolt suitable for locking the holder on the support rail.

4. The radiation protection arrangement according to claim 3, wherein the handle is capable of being pivoted into a first position and wherein, in the first position, the holder on the support rail is not locked by the locking bolt.

5. The radiation protection arrangement according to claim 4, wherein, in the first position, the at least one handle is arranged in a position at an angle of from 10° to 70° to the longitudinal direction of the longitudinal profile of the holder with regard to the upper side of the longitudinal profile.

6. The radiation protection arrangement of claim 5 wherein at least one handle is arranged in a position at an angle of 30°.

7. The radiation protection arrangement according to claim 3, wherein the at least one handle is capable of being pivoted into a second position and wherein in the second position the at least one locking bolt locks the holder on the support rail.

8. The radiation protection arrangement according to claim 7, wherein, in the second position, the at least one handle is arranged in a position at an angle of approximately −90° to the longitudinal direction of the longitudinal profile of the holder with regard to the upper side of the longitudinal profile.

9. The radiation protection arrangement according to claim 7, wherein the handle has at least one latching recess which is capable of retaining the handle in the first and/or the second position up to a specific pivot force.

10. The radiation protection arrangement according to claim 3, wherein the holder comprises a receptacle, wherein the longitudinal profile has a contact face and, when the radiation protection arrangement is attached to the support rail, the contact face of the longitudinal profile partially rests on the upper side of the support rail, and wherein the at least one locking bolt is situated in the receptacle which is arranged at the contact face of the longitudinal profile such that the at least one locking bolt is situated at a particular distance A relative to the contact face.

11. The radiation protection arrangement according to claim 10, wherein the distance A is arranged such that when the radiation protection arrangement is attached to the support rail, the locking bolt in the locked state extends partially along the bottom of the support rail.

12. The radiation protection arrangement according to claim 10, wherein the distance A is arranged such that when the radiation protection arrangement is attached to the support rail, the locking device in the locked state is pressed against the bottom of the support rail.

13. Radiation The radiation protection arrangement according to claim 1 with at least one transverse lamella attached to the fastening device, wherein the transverse lamella is designed and/or arranged such that the transverse lamella overlaps with an upper part of the lamella.

14. The radiation protection arrangement according to claim 1, wherein the at least one handle is attached to the short side of the longitudinal profile.

15. The radiation protection arrangement according to claim 1, wherein the holder has a bearing in which the handle is pivotably mounted.

16. The radiation protection arrangement according to claim 1, wherein the handle comprises an anti-sliding device which is capable of preventing a hand from sliding off the handle in the second position.

17. A radiation protection arrangement, for attaching to at least one support rail which is attached to one or more sides of a treatment table, comprising a holder which can be attached to the support rail and attached to at least one detachable lamella at different positions, wherein the radiation protection arrangement is combined with a radiation protection arrangement according to claim 1.

18. The radiation protection arrangement according to claim 17, wherein the holder has at least one bore and the at least one detachable lamella has at least one pin and wherein the at least one pin is insertable into the at least one bore.

19. The radiation protection arrangement according to claim 17, wherein the at least one detachable lamella has at least one U-shaped holding means, and wherein the at least one U-shaped holding means is attachable to the holder.

20. The radiation protection arrangement of claim 19, wherein the U-shaped holding means is made from plastic.

21. The radiation protection arrangement of claim 12 wherein the locking device in the locked state is pressed against the bottom of the support rail at an angle of 45° to the normal of the bottom of the support rail.

22. The radiation protection arrangement of claim 1 wherein the radiation comprises X-ray radiation.

23. The radiation protection arrangement of claim 1 wherein the anti-sliding device is formed as a projection at the free end of the handle.

* * * * *